(12) United States Patent
Hirano et al.

(10) Patent No.: US 6,501,985 B1
(45) Date of Patent: Dec. 31, 2002

(54) SYSTEM FOR RECOVERING MOTOR FUNCTION AFTER SPINAL CORD INJURY

(75) Inventors: Shinnosuke Hirano, Kanagawa-ken (JP); Stanly Tsuyoshi Ohnishi, Radnor, PA (US); Saburo Hidaka, Fukuoka-ken (JP); Yoshizo Okamoto, Fukuoka-ken (JP)

(73) Assignee: Kohgen Kizai Kabushiki Kaisha, Kanagawa (JP)

( * ) Notice: Subject to any disclaimer, the term of this patent is extended or adjusted under 35 U.S.C. 154(b) by 0 days.

(21) Appl. No.: 09/417,481

(22) Filed: Oct. 13, 1999

(30) Foreign Application Priority Data

Oct. 14, 1998  (JP) .......................... 10-292005

(51) Int. Cl.[7] .................................. A61N 1/20
(52) U.S. Cl. ......................................... 607/2
(58) Field of Search ............................. 607/2, 43, 75, 607/117, 152

(56) References Cited

U.S. PATENT DOCUMENTS 4,846,178 A * 7/1989 Fuxue et al. ................ 607/75
4,893,626 A * 1/1990 Henley et al. ............... 607/2
5,836,997 A * 11/1998 Hirano ....................... 607/75

FOREIGN PATENT DOCUMENTS

| JP | 8-224316 | 9/1996 |
| JP | 9-322944 | 12/1997 |

OTHER PUBLICATIONS

"Enhanced Spinal Cord Regeneration in Lamprey by Applied Electric Fields," Science, vol. 213, Aug. 7, 1981, Richard Borgens et al., pp. 611–617.

* cited by examiner

Primary Examiner—Jeffrey R. Jastrzab
(74) Attorney, Agent, or Firm—Rader, Fishman & Grauer, PLLC

(57) ABSTRACT

There is disclosed a system for recovering motor function after spinal cord injury, which has a mat having a first sheet made from a semi-conductive or insulating material and with a volume resistivity of less than $10^4$ Ω·cm and a second sheet made from a semi-conductive or insulating material, laminated on the first sheet and with a volume resistivity of $10^4$ Ω·cm or more; an electric power source; an electrical circuit to apply 25–800 VDC to the first sheet; and a control unit for the system. A person with spinal cord injury is made contact with the mat, so as to put his body in electrostatic field to be induced on the mat.

3 Claims, 3 Drawing Sheets

SYSTEM FOR RECOVERING MOTOR FUNCTION AFTER SPINAL CORD INJURY

BACKGROUND OF THE INVENTION

1. Field of the Invention

The present invention relates to a system for recovering motor function after spinal cord injury, by subjecting a patient to electrostatic field.

2. Related Arts

The spiral cord injury has often been seen in athletes' injury and victims of car accidents. Since the patients are sometimes paralyzed and require a life-long care, a method of enhancing the motor recovery has been strongly desired. While biochemical and molecular biological approaches have been vigorously tried, but a study to find physical means to enhance the motor function recovery has been delayed.

Borgens, R. B. et al. report to the effect that completely severed spinal cord of a lamprey was regenerated in 2 months by application of 10 $\mu$A of DC current across the severed section ["Science", Vol. 213, pages 611–617 (1981)]. They described that the electric current had a direct effect on the nerve regeneration, but the molecular mechanism has not been elucidated.

In Japan, health benefits of high-voltage electrostatic fields have been known, and several commercial devices to produce such a field have been proposed and sold in the market for the past decades. According to such a device, the electrostatic field has been caused on a single layer sheet or mat of a synthetic resin material such as polyvinyl chloride by applying DC voltage of several hundreds to several thousands to the mat. It has been said that these mats are effective for patients with muscle pain, arthritis and certain chronic diseases.

However, the device utilizing static electricity requires incidental facilities for increasing voltage such as a transformer, so that it becomes larger in size to increase manufacturing and running costs. Further, the device has a serious disadvantage of that a user might get a shock of electricity due to leakage thereof.

In order to overcome the disadvantages of the device utilizing static electricity, one of the researchers in the assignee company has studied to find facts that static electricity can be stably induced, if laminating a first sheet of conductive or semi-conductive layer having a volume resistivity of less than $10^4$ $\Omega$·cm to a second sheet of conductive or insulation layer having a volume resistivity of $10^4$–$10^{12}$ $\Omega$·cm, and applying voltage to the first sheet, that a value of electrostatic voltage can be made higher level, if the difference in volume resistivity of the first and second sheets is set to $10^4$ $\Omega$·cm or more, and that a possibility of the dangerous shock due to leakage of electricity can be avoided by setting voltage and current to be applied to the first sheet to 25–800 VDC and 0.8 mA, respectively. The assignee company has filed a patent application in Japan on the invention, based on such findings [Japanese Patent 8-224316(A)]. According to the device disclosed in the specification for the Japanese patent application, it is possible to induce electrostatic voltage of –3.05KV on the second sheet having a volume resistivity of $10^7$ $\Omega$·cm by applying 800 VDC to the first sheet having a volume resistivity of $10^3$ $\Omega$·cm, and this device is suitable for relieving headache and shoulder stiffness as well as preventing and curing insomnia and chronic constipation.

However, the uses of relieving headache and shoulder stiffness as well as preventing and curing insomnia and chronic constipation are not definite and it is difficult to confirm a concrete utility of such a device, since an effect of spiritual security giving to the user of the device cannot be neglected on generation of the utility.

By using the device, one of the inventors have energetically studied and investigated on influence(s) of the static electricity to a living body through tests using experimental animals to seek a new applicable use(s) of it. As a result, it has been unexpectedly found that the device is useful for inhibiting a decrease in an amount of bone to prevent and cure osteoporosis and also inhibiting an appetite without increasing a body weight to prevent and cure obesity. The related patent application was filed in Japan in the name of assignee company [Japanese Patent 9-322944(A) which corresponds to U.S. Pat. No. 5,836,997].

The inventors have further studied on influence of the static electricity to a living body through tests using experimental animals to find that the application of electrostatic fields effects on the recovery of rat spinal cord injury produced by a weight drop impulse on the exposed cord, so that the invention was established.

SUMMARY OF THE INVENTION

Therefore, an object of the invention is to provide a system for recovering motor function after spinal cord injury by putting a body of patient in an electrostatic field, for instance contacting his body with a mat which is inducing static electricity.

According to the invention, the object is attained by a system for recovering the motor function after spinal cord injury, which comprises a mat essentially consisting of a first sheet made from a semi-conductive or insulating material and having a volume resistivity of less than $10^4$ $\Omega$·cm and a second sheet made from a semi-conductive or insulating material, laminated on said first sheet and having a volume resistivity of $10^4$ $\Omega$·cm or more; an electric power source having an electrical circuit to apply 25–800 VDC to said first sheet; and a control unit for said electric power source.

The first and second sheets are made from one of silicone rubber, natural rubber, nitril rubber and synthetic resin material (such as polyvinyl chloride and polyurethane resin) and carbon.

It is preferable to set the electrical input to the first sheet as 800 VDC and 0.8 mA.

DETAILED DESCRIPTION OF PREFERRED EMBODIMENT

In the first place, a device constituting the system according to the invention shall be explained with reference to FIGS. 1 and 2.

Figure 1:
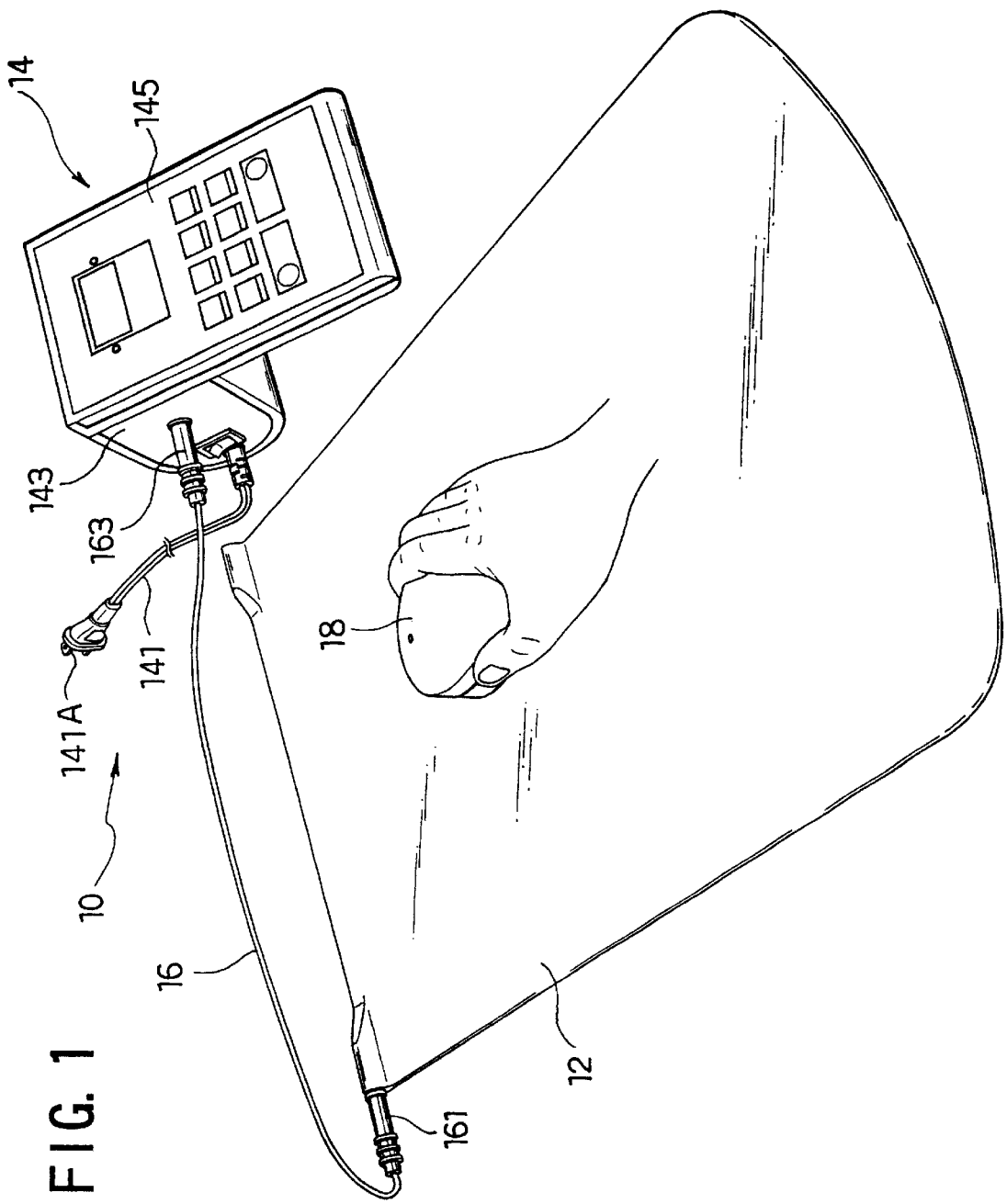
FIG. 1 is a schematic and perspective illustration showing a system according to the invention.

FIG. 1 shows the device 10. The device 10 comprises a mat 12, a control unit 14, a cable 16 with jacks 161 and 163 connecting the mat 12 with the control unit 14, and a sensor 18 for static electricity. The control unit 14 has a cable 141 with a plug 141A which is to be electrically connected with a plug receptacle (not shown) for commercial voltage source, a main part 143, and an operating board 145.

Figure 2:
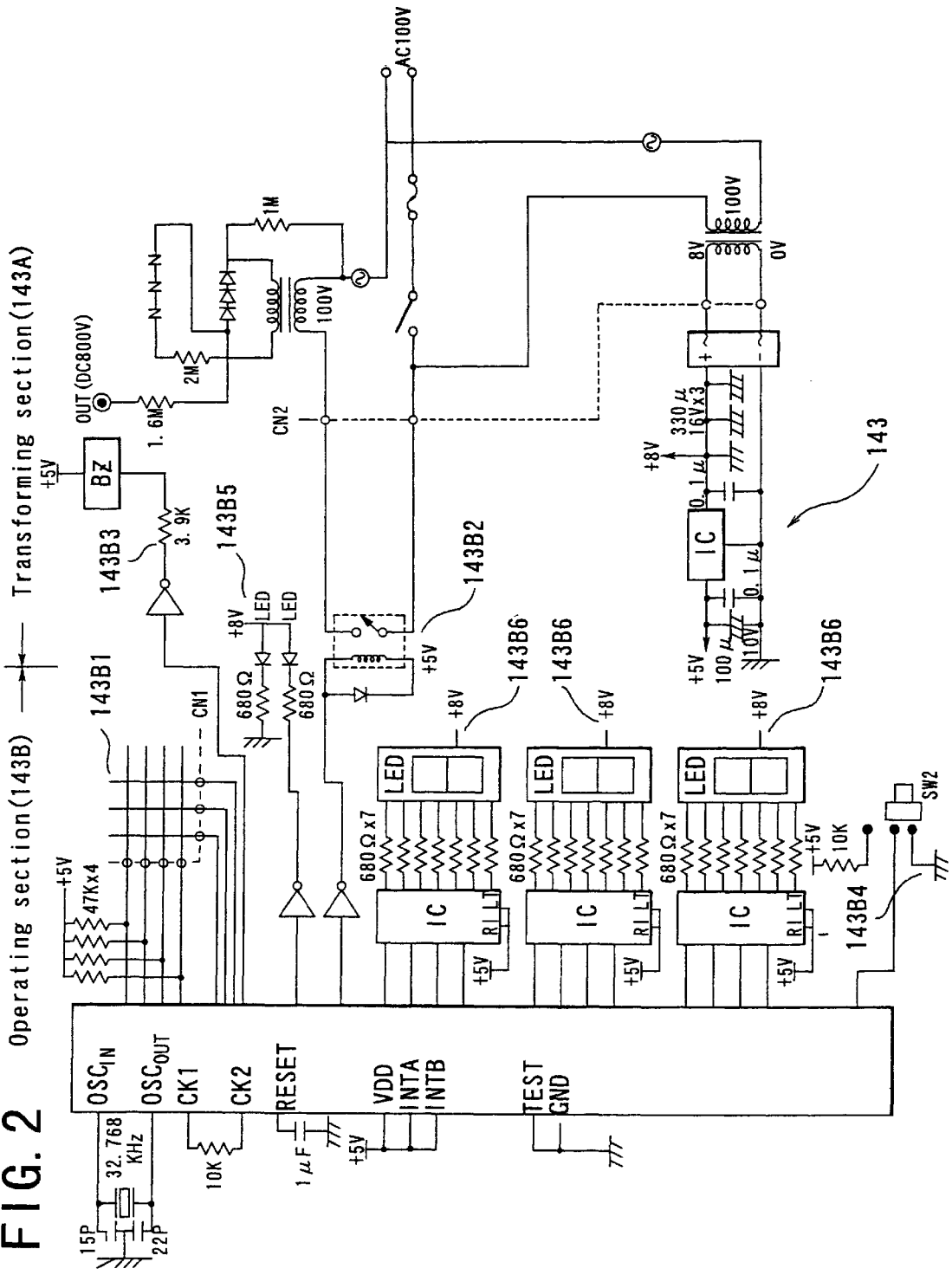
FIG. 2 shows an electrical circuit for a transforming section and operating section in a control unit of the system shown in FIG. 1.

FIG. 2 shows an electric circuit for the main part 143 which has a transforming section 143A and an operating section 143B. The transforming section 143A transforms 100 VAC from the commercial voltage source into 800 VDC which appears at a terminal described as "OUT" and supplied to the mat 12 through the connecting cable 16, 5 VDC which is supplied to a basic operating circuit 143B1, an electromagnetic circuit 143B2, a buzzer circuit 143B3 and a timer mode switching circuit 143B4, and 8 VDC which is supplied to a lamp circuit 143B5, and timer and display circuits 143B6.

The voltage increased to 800 VDC by the transforming section 143A and appeared at the terminal "OUT" is applied to a first sheet (not shown) of the mat 12 to uniformly generate static electricity on surface of a second sheet (not shown) laminated on the first sheet. In this case, a value of current should be set to a small one, for instance 0. 8 mV, to avoid leakage and shock of electricity.

Results shown in following Table 1 were obtained, when the first and second sheets having various volume resistivity were laminated and 800 VDC (0.8 mA) was applied to the first sheet to check electrostatic voltage induced on the sheets.

TABLE 1

| Volume resistivity ($\Omega \cdot cm$) | | Electrostatic voltage (-KV) | |
| --- | --- | --- | --- |
| First sheet | Second sheet | First sheet | Second sheet |
| $10^3$ | $10^7$ | 0.01 | 3.05 |
| $10^2$ | $10^{10}$ | 0.01 | 2.30 |
| $10^5$ | $10^{10}$ | 0.02 | 0.87 |
| $10^5$ | $10^6$ | 0.03 | 0.03 |

It is apparent from the results shown in Table 1 that the volume resistivity of the first and second sheets should be set to $10^2$–$10^4$ and $10^6$–$10^{10}$ $\Omega \cdot cm$, respectively, that difference in the volume resistivity of the first and second sheets should be set to $10^4$ $\Omega \cdot cm$ or more, and that such a case is best that the volume resistivity of the first and second sheets is $10^3$ and $10^7$ $\Omega \cdot cm$, respectively.

Next, the invention will now be further explained in more detail and concretely with following Test Example.

TEST EXAMPLE (1) Method of Creating Spinal Cord Injury

A weight drop method was used. Namely, a steel bearing ball (weight: 5.6 g—about 0.012 pounds—, diameter: 11 mm—7/16 inches—) made a friction-free was free dropped of 5 cm to hit a light weight impounder. The impounder had a tip diameter of 0.26 mm which was resting on the exposed spiral cord of each experimental animal to create injury.

(2) Experimental Animals

Sprague Dawley female rats (body weight of 250–275g) were purchased and anesthetized by i. p. injection of Nembutal (Na-Pentobarbital, 50 mg/kg). Each of the anesthetized animals was placed in ventral recumbency on a small board. The dorsal laminectomy was performed at T9 site and the contusion injury was applied while the animal was staying on the board, in the manner as described in said Item (1).

(3) Motor Function Score Measurement

Such three different tests of walking ability, balancing on a rod, and ability to stay on or climb up an inclined plate covered with rubber were carried out. Evaluations were judged with following standards. Therefore, total motor function score ranges from 0 to 9.

(a) Walking Ability on Flat Surface

| Motor function score | State |
| --- | --- |
| 0 | Difficult to support body weight by hind limbs. |
| 1 | Able to support body weight, but can not walk. |
| 2 | Able to walk by showing remarkable obstacle in hind limbs. |
| 3 | Walks in smooth. |

(b) Walking Ability On Horizontally Arranged Rod (diameter: 1.25 inches)

| Motor function score | State |
| --- | --- |
| 0 | Can not grasp the rod by hind limbs. |
| 1 | Trying to grasp the rod by hind limbs. |
| 2 | walking with use of hind limbs, but with difficulty. |
| 3 | Able to walk on the rod. |

(c) Walking Ability On Inclined Plate Covered With Rubber

| Motor function score | State |
| --- | --- |
| 0 | Slip-down in inclination angle of 55 degrees. |
| 1 | Staying for 10 seconds or more, in case of inclination angle of 55 degrees. |
| 2 | Climbing up the plate having inclination angle of 55 degrees. |
| 3 | Climbing up the plate having inclination angle of 60 degrees. |

(4) Device for Applying Electrostatic Field to Animals

The device as shown in FIGS. 1 and 2 was used. A mat of the device is three-layered one consisting of a first or middle sheet of a silicone rubber with carbon black (manufactured and sold by Toshiba Silicone Co., Ltd. as "XE23-B1717") having a volume resistivity of about $10^3$ $\Omega \cdot cm$, a second or upper sheet of a silicone rubber (manufactured and sold by Toray, Dow Corning and Silicone Co., Ltd. as "SE4635U") having a volume resistivity of about $10^7$ $\Omega \cdot cm$) and a third or lower sheet of a silicone rubber (manufactured and sold by Toshiba Silicone Co., Ltd. as "TSE221-3U") having a volume resistivity of more than $10^{12}$ $\Omega \cdot cm$).

Specification of the device is as follows.

(i) Rated voltage: 100 VAC
(ii) Output voltage: 800 VDC
(iii) Frequency: 50/60 Hz
(iv) Consuming power: 6 W
(v) Body portion:
  Size: 111 (height)×104 (width)×177 (depth) mm
  Weight: 1,100 g (vi) Mat portion:
   Size: 3 (thickness)×500 (length)×350 (width) mm
   Weight: 760 g
The device stably induces electrostatic voltage of −3.05 KV on the mat.

(5) Method of Application of Electrostatic Fields
The animals were classified into following 3 groups.
(a) Test Group (14 Animals):
   The animals, each of them is artificially created spinal cord injury and applied electrostatic fields every day for the testing time period of 35 days.
(b) Control Group (14 Animals):
   The animals, each of them is artificially created spinal cord injury, but not applied the electrostatic fields.
   (c) Sham Group (10 Animals):
   The animals, each of them was anesthetized and subjected to a sham operation causing no spinal cord injury, but not applied the electrostatic fields.
   The rats in each group were housed in a polyethylene shoe-box type cage, the cage was placed on the rubber mat of the device, and a standard rat food and water were given ad libitum. To the rubber mat, on which the cage accommodating the animals in the test group was placed, applied the electrostatic field for 2 hours every day. The cages accommodating animals in the control and sham groups were also placed on the rubber mat for 2 hours every day, but applied no electrostatic fields. The motor function tests and the electrostatic field application were done around same time every day; the tests were done around 1:00 p.m. and the field application was started around 2:00 p.m.

(6) Statistical Analysis
   The statistical significance was evaluated by two-way ANOVA with Scheffe's test using a computer software. The difference of $p<0.05$ was considered to be significant.

(7) Results
   (A) Motor Function In Control and Sham Groups
   A steel bearing ball with diameter of 11 mm (7/16 inches) and weight of 5.6 g (about 0.012 pounds) was used for creating the spinal cord injury. In the control group (no electrostatic field application), the steel ball drop from 5 cm height produced complete paralysis on the first day, but the rat started to natural recover from the first week after injury, and in 5 weeks, the motor function score recovered and reached almost a plateau value of 5.2±0.7, as shown by open circles in FIG. 3.

Figure 3:
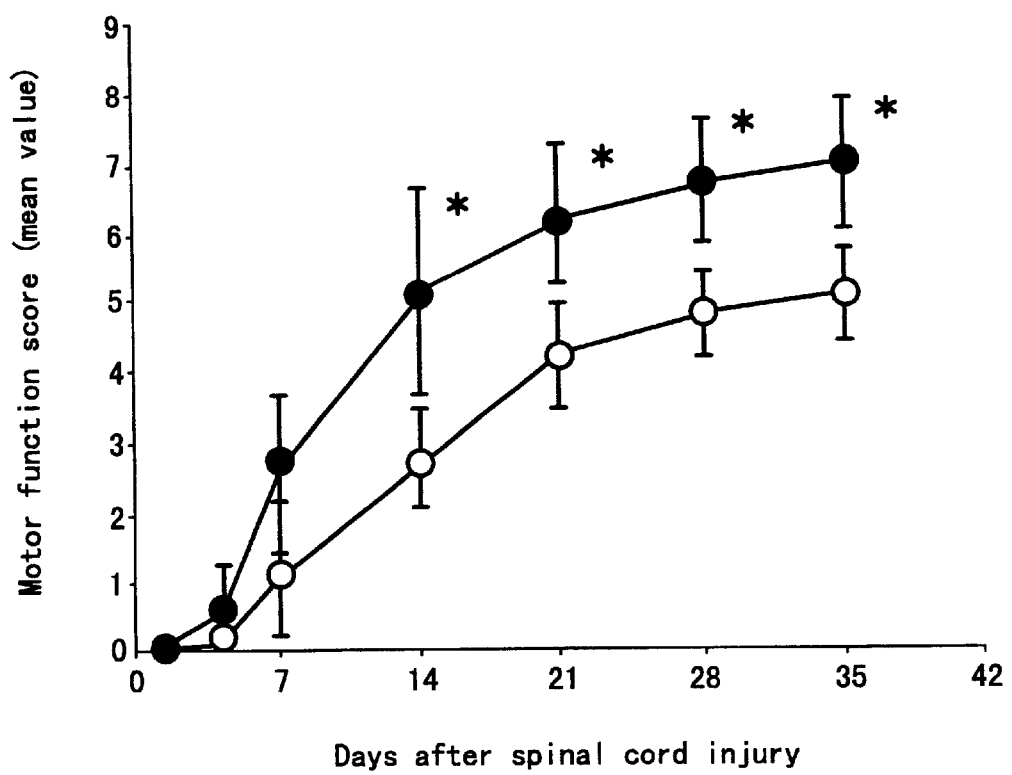
FIG. 3 is a graph showing a relation between breeding period of time and mean value of motor function score on a test group which was exposed to electrostatic field after artificially caused spiral cord injury and a control group which was artificially caused spiral cord injury but not exposed to the electrostatic field.

In the animals in the sham group (the sham operation was performed, but no spiral cord injury was applied), the motor score was the perfect score of 9 (data not shown in FIG. 3).

(B) Spontaneous Urination
   It has been known that compression of the bladder is required twice a day for several days after spinal cord injury to cause urination, when the experimental animals are male rats. However, in this experiment where female rats were used, only 10% of animals required the compression of bladder for the first few days after the injury. Most of the rats urinated spontaneously.

(C) Effects of Electrostatic Field on Motor Function Recovery After Spinal Cord Injury
   The effect of the application of electrostatic field on the recovery is shown by black circles in FIG. 3. As apparently seen from the Figure, it started to recover from fourth day, and kept recovering faster than the control rats shown by open circles in the Figure. The difference from the control rats become significant from 14th day. At 35th day, the motor score reached 7.4±0.9. The difference was significant ($p<0.05$).

What is claimed is:
1. A method for recovering motor functions after spinal cord injury, said method comprising:
   providing a mat including of a first sheet made from a semi-conductive or insulating material and having a volume resistivity of less than $10^4$ Ω·cm and a second sheet made from a semi-conductive or insulating material, laminated on said first sheet and having a volume resistivity of $10^4$ Ω·cm or more, and an electric power source having an electrical circuit to apply 25–800 VDC to said first sheet, and a unit for controlling said electric power source;
   applying a voltage to said first sheet, thereby inducing an electrostatic field;
   applying the electrostatic field to a body of a patient.
2. A method as recited in claim 1, wherein said step of applying a voltage to the first sheet comprises a step of applying 800 VDC with 0.8 mA, thereby inducing an electrostatic voltage of −3.05 KV on said second sheet.
3. A method as recited in claim 1, wherein said step of providing the mat comprises a step of providing the first and second sheets with a volume resistivity of $10^3$ and $10^7$ Ω·cm, respectively.

* * * * *